United States Patent [19]

McKirdy et al.

[11] Patent Number: 4,612,808

[45] Date of Patent: Sep. 23, 1986

[54] CONTACT ULTRASONIC PROBE HOLDERS

[75] Inventors: Bruce J. McKirdy, Summer Town; Ashley G. Cooper, Warrington, both of England

[73] Assignee: United Kingdom Atomic Energy Authority, London, England

[21] Appl. No.: 703,021

[22] Filed: Feb. 19, 1985

[51] Int. Cl.⁴ ............................................. G01N 29/04
[52] U.S. Cl. ........................................ 73/622; 73/623; 73/639; 73/640
[58] Field of Search ................. 73/622, 623, 637, 638, 73/639, 640, 588

[56] References Cited

U.S. PATENT DOCUMENTS

| | | | |
|---|---|---|---|
| 3,308,652 | 3/1967 | Appel et al. | 73/640 |
| 3,828,609 | 8/1974 | Furon et al. | 73/622 |
| 4,194,400 | 3/1980 | Staff | 73/623 |
| 4,434,660 | 3/1984 | Michaels et al. | 73/637 |

*Primary Examiner*—Anthony V. Ciarlante
*Attorney, Agent, or Firm*—William R. Hinds

[57] ABSTRACT

An ultrasonic probe for inspecting a weld between a cylinder (C) and a pipe (P) is caused to move in a holder at the end of an arm (11) pivoted at a point on the axis (Z) of the pipe so that the line (12) of transmission from probe penetrates the weld and, when projected beyond the weld, intersects the axis (Z) of the pipe (P) for all positions of the arm.

13 Claims, 4 Drawing Figures

CONTACT ULTRASONIC PROBE HOLDERS

BACKGROUND OF THE INVENTION

This invention relates to contact ultra-sonic probe holders and is suitable for the ultra-sonic inspection of components having irregular surface geometry.

For inspections of this kind it is often desirable that the ultra-sonic beam travels into the components in a direction which is independent of the shape of the surface under the probe holder. This situation arises in the case of the inspection of a weld formed when a circular pipe is joined by welding with a circular vessel, the axes of pipe and vessel being at right angles. Welds of this form appear in the nuclear art. The probe holder also has application in the inspection of other complex welds.

It is an object, when inspecting pipe/vessel welds, to direct an ultra-sonic beam from a probe in a direction so that the line of the beam (when projected) intersects the axis of the pipe. The direction of the beam is then such as to make a right angle with the circumferential direction vector at the weld at all positions in the weld. If the probe is mounted on a gimbal holder or universal joint arrangement (see for example GB-PS-No. 1404471) so that the surface of the probe remains in contact with the surface of the vessel, and the holder is mounted at the end of an arm which rotates about a point on the axis of the pipe which lies inside the vessel then at four angles of rotation only of the arm (namely 0°, 90°, 180° and 270°) does the projected beam intersect the axis of the pipe. At other angles the required intersection is not attained.

FEATURES AND ASPECTS OF THE INVENTION

To overcome this disadvantage, in accordance with the invention, the gimbal mounted probe is provided with a mechanical linkage to impose a rotation on the probe by virtue of, and whilst maintaining surface contact with, the vessel which compensates for the deviation of the projected beam from intersecting the axis of the pipe. This rotation is preferably provided by arranging that the probe is mounted in a head having a pair of inclined slots into which respective stub axles are inserted, the stubs being carried on an extension of the arm which rotates about a point on the axis of the pipe.

DESCRIPTION OF THE DRAWINGS

The invention will now be described further with reference to the accompanying drawings in which.

DESCRIPTION OF THE PREFERRED EMBODIMENT

Figure 1:
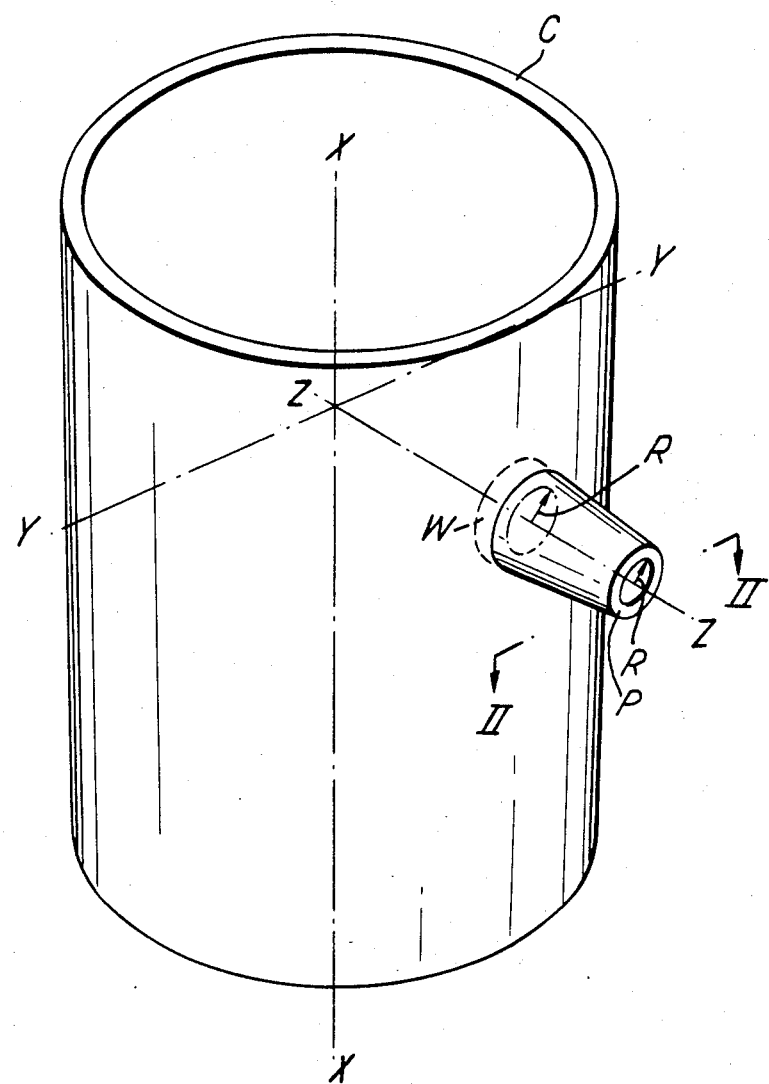
FIG. 1 is a perspective view of a pipe welded to a cylinder.

In FIG. 1 a pipe P is shown welded to a cylinder C (the diameter ratios are typically 1:5), at a weld W. The three coordinate axes X,Y and Z are shown together with a pipe internal radius R.

Figure 2:
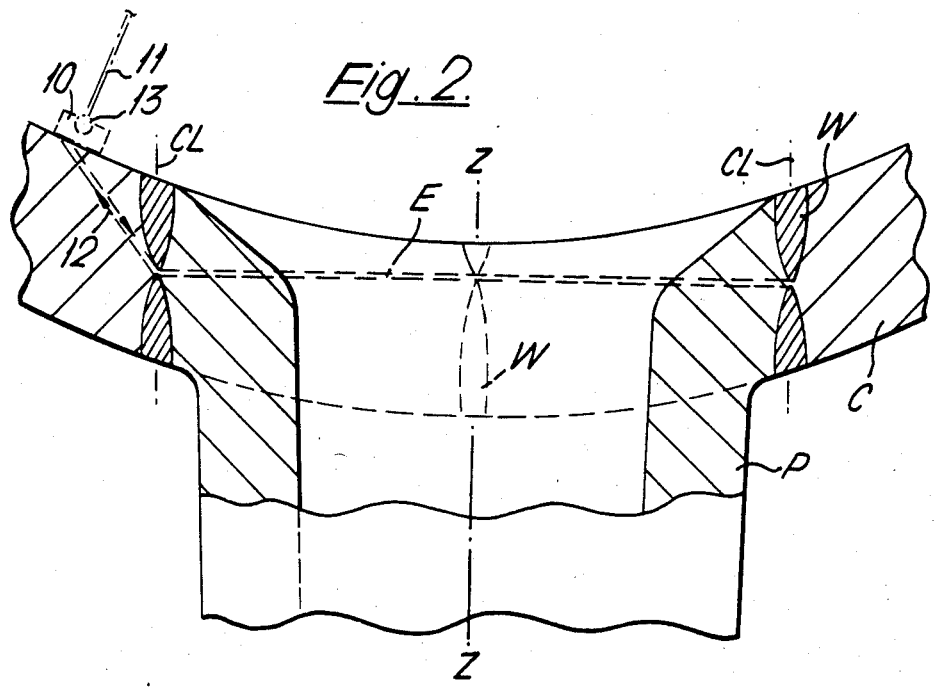
FIG. 2 is a horizontal section on the plane indicated by II—II of FIG. 1.

FIG. 2 shows the nature of the weld to be inspected. The cylinder C and pipe P have engaging edges E and the weld W extends as an inward part and outward part from the edges E. The weld can be regarded as having a centre line CL which lies on a cylindrical surface coaxial with axis Z. The edge E lies at the rim of a cylinder and hence the inward and outward parts of the weld vary in depth as exemplified by the dash line weld W shown on the axis Z.

An ultrasonic probe 10 for inspecting the weld is shown mounted at the end of an arm 11 so that the probe is in contact with the internal surface of the cylinder C. The arm is pivoted at the point of intersection of the Z and X axes and has freedom to move the probe 10 around the inside surface of the cylinder so that transmissions 12 can be used to inspect the weld. The probe 10 is mounted on the arm 11 at a gimbal 13 (described in detail with FIGS. 3 and 4) so that as arm 11 is rotated the probe follows the surface of the cylinder so that the beam is directed into the weld W. (It is convenient to mention at this point that if gimbal 13 were of conventional construction then at all positions other than 0°, 90°, 180° and 270° of rotation of arm 11 the beam of the probe would not, when projected, intersect the axis Z of the pipe P). The present invention avoids this.

Figure 4:
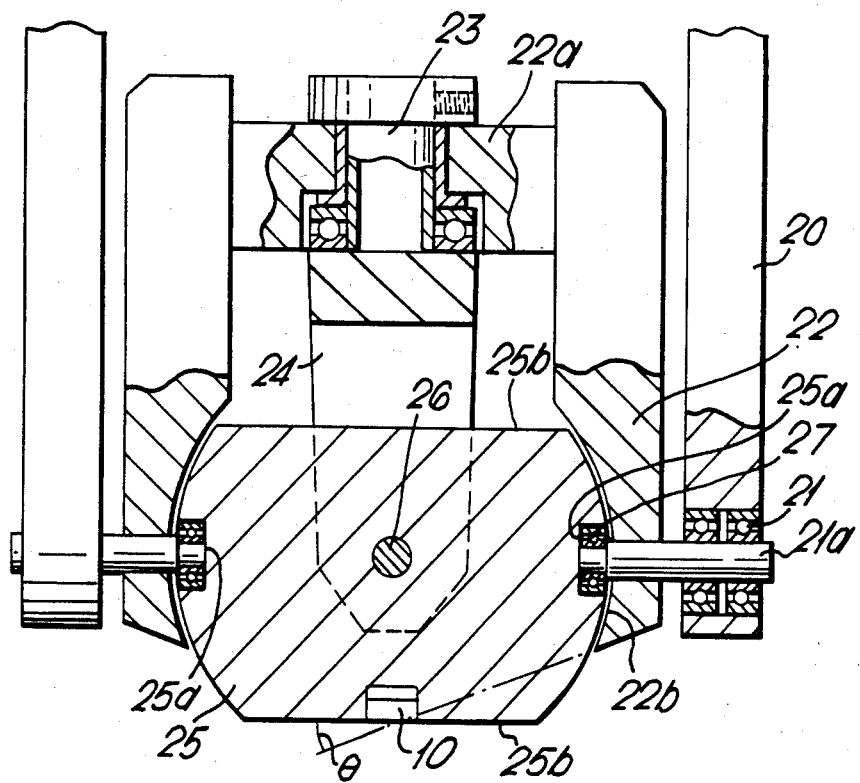
FIG. 4 is a vertical sectional view in the direction indicated by line IV—IV of FIG. 3.
Figure 3:
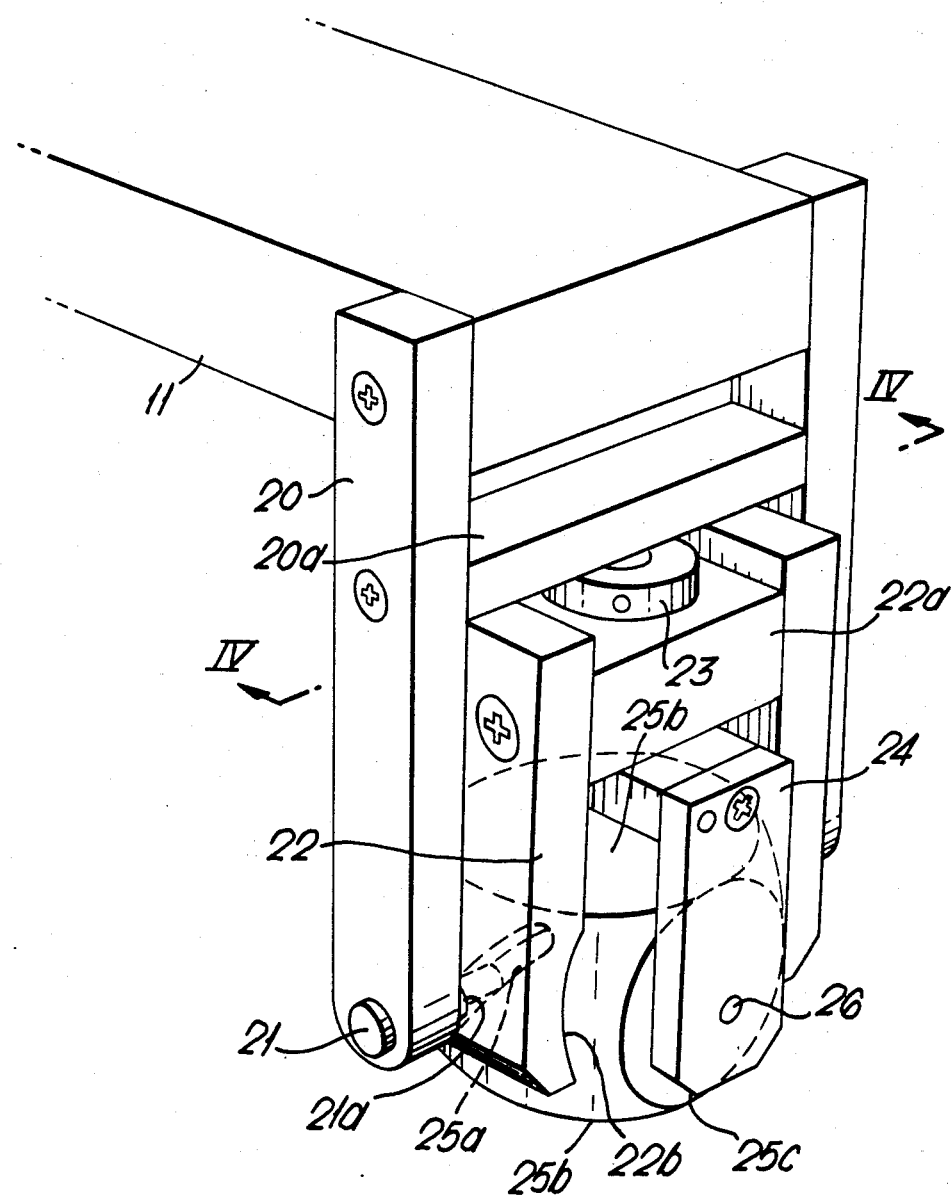
FIG. 3 is a perspective of a gimbal mounted probe in accordance with the invention.

In FIGS. 3 and 4 the arm 11 is shown with a downward extension 20 having a cross strengthener 20a and bearings 21 at the lower end of extension 20. The bearings each support a stub axle 21a. The gimbal 13 comprises an outer frame 22 with a cross strut 22a, a pivot 23 in cross-strut 22a, an inner frame 24 mounted on pivot 23 and carrying a "ball" 25 mounted on a pivot 26 in the inner frame 24.

The ball 25 has upper and lower flat surfaces 25b and front and rear flat surfaces 25c. The ball also has a pair of inclined slots 25a into which the stub axles 21a enter. The axles 21a terminate at bearings 27 in the slots 25a, they are fixed to the frame 22 where they penetrate it and they rotate in bearings 21 in arm extensions 20. The ultrasonic probe 10 is mounted in the lower flat surface 25b. The curved surfaces of the ball (which have the slots 25a) engage in spherical sockets 22b in the frame 22. The slots 25a lie in a plane which is inclined to the flat surfaces 25b and inclined to the axis of pivot 26.

In use, the lower flat surface 25b of the ball follows the surface of the cylinder C as the arm 11 is caused to rotate and in doing so adopts a rotation about an axis normal to the flat surface 25b and about the axis of the pivot 26 as determined by the stub axles in the slots 25a. This causes the beam from the probe 10 (when projected) to always intersect the axis Z of the pipe P.

As the ball moves over the surface of the cylinder C the aspect of the undersurface 25b alters as shown by the angle $\theta$ and the slots 25a impose a rotation on the ball and keep the beam from the probe in the desired direction.

Other, but similar, probe mountings can be provided to ensure that an ultrasonic inspection beam "looks" in other predetermined directions and not necessarily towards the axis of pipe P. For example, the beam could look in a direction which is tangential to the cylindrical surface coaxial with axis Z.

The weld could also be inspected by arranging for the probe 10 to be moved over the external surface of the cylinder C.

We claim:

1. A probe holder in which a probe is mounted on a gimbal so that the probe can maintain contact with a curved surface whilst being moved at the end of an arm pivoted about an axis, in which the gimbal is provided with means for effecting a mechanical linkage to impose a rotation on the probe by virtue of, and whilst maintaining, surface contact, which rotation sustains the sighting of the probe in a desired direction, said rotation of said probe being about an axis normal to said surface.

2. A probe holder as claimed in claim 1 in which the probe is mounted in a head having a pair of inclined slots into which respective stub axles are inserted, the axles being carried on an extension of said arm.

3. A probe holder as claimed in claim 2 in which the head is of spherical shape with southern polar cap removed to leave a surface which carries the probe and the slots are inclined to the equator of the spherical surface.

4. A probe holder as claimed in claim 3 in which the arm is mounted on the axis of a pipe making a normal junction with a cylinder at a weld and the arm has an extension with gimbal pivot bearings for the gimbal; and the gimbal comprises an outer frame pivotable on the bearings and an inner frame pivot with an inner frame mounted on that pivot; and the spherical-shaped head is rotatable on an axle in the inner frame, said axle defining said axis of rotation, said head being confined by sockets in the outer frame and confined by stub axles on the axis of the gimbal pivot bearings which penetrate into the slots inclined to the equator of the spherical surface.

5. A method of inspecting a weld between a pipe and cylinder comprising moving an ultrasonic probe in a holder as claimed in claim 4 along the surface of the cylinder whilst confining it to move at the end of an arm which is pivoted about the axis of the pipe so that radiation from the probe is incident upon the weld at an angle such that the line of the radiation, when projected beyond the weld, always extends in a predetermined direction.

6. A method of inspecting a weld between a pipe and cylinder comprising moving an ultrasonic probe in a holder as claimed in claim 2 along the surface of the cylinder whilst confining it to move at the end of an arm which is pivoted about the axis of the pipe so that radiation from the probe is incident upon the weld at an angle such that the line of the radiation, when projected beyond the weld, always extends in a predetermined direction.

7. A method of inspecting a weld between a pipe and cylinder comprising moving an ultrasonic probe in a holder as claimed in claim 3 along the surface of the cylinder whilst confining it to move at the end of an arm which is pivoted about the axis of the pipe so that radiation from the probe is incident upon the weld at an angle such that the line of the radiation, when projected beyond the weld, always extends in a predetermined direction.

8. A method of inspecting a weld between a pipe and cylinder comprising moving an ultrasonic probe in a holder as claimed in claim 1 along the surface of the cylinder whilst confining it to move at the end of an arm which is pivoted about the axis of the pipe so that radiation from the probe is incident upon the weld at an angle such that the line of the radiation, when projected beyond the weld, always extends in a predetermined direction.

9. A method as claimed in claim 5 in which said predetermined direction intersects said axis.

10. A method as claimed in claim 9 in which the axis is the axis of the pipe.

11. Apparatus for projecting a beam of ultrasonic energy into a body having a curvilinear contour, said apparatus comprising a probe for producing said beam; a probe holder carrying the probe and presenting the probe for contact with said body; means for mounting the probe holder and traversing the probe holder over said body with the probe in contact with said curvilinear contour; said probe holder comprising:
  (a) a ball element carrying the probe;
  (b) gimbal means comprising a U-shaped inner frame having side legs between which the ball element is located and a U-shaped outer frame having side legs between which the inner frame is located;
  (c) first pivot means interconnecting the ball element with the side legs of the inner frame;
  (d) second pivot means interconnecting the side legs of the outer frame with the mounting means, said first and second pivot means defining respective first and second axes which are mutually orthogonal with respect to one another;
  (e) third pivot means interconnecting the inner and outer frames whereby the inner frame is movable angularly relative to the outer frame about a third axis perpendicular to said first and second axes; and means for mechanically linking said outer frame and the ball element and operable automatically, in response to angular movement of said ball element about said first and second axes as the ball element traverses over said curvilinear contour, to effect compensating angular movement of the ball element about the third axis whereby a predetermined relationship between the direction of said beam and the mounting means is maintained.

12. Apparatus as claimed in claim 11 in which said means for mechanically linking the outer frame and the ball element comprise pin and slot means.

13. Apparatus as claimed in claim 12 in which said pin and slot means comprise slots formed in the ball element at diametrically opposite sides thereof and pins coaxial with said second pivot means, the slots each extending above and below a plane containing said first and second axes.

* * * * *